US00PP31583P2

(12) United States Plant Patent
Olesen et al.

(10) Patent No.: US PP31,583 P2
(45) Date of Patent: Mar. 24, 2020

(54) *CLEMATIS* PLANT NAMED 'EVIPO099'

(50) Latin Name: *Clematis viticella*
Varietal Denomination: Evipo099

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,895

(22) Filed: Sep. 10, 2018

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
See application file for complete search history.

(56) References Cited

PUBLICATIONS http://grenethplants.nl/wp-content/uploads/2017/06/Catalogue-2017_18-ENG_GP-Digital.pdf, downloaded Jun. 20, 2019.*
UPOV hit on *Clematis* plant named 'Evipo099', QZ PBR 20172276, filed Sep. 19, 2017.*

* cited by examiner

*Primary Examiner* — Anne Marie Grunberg

(57) ABSTRACT

A new *Clematis* plant with a compact growth habit, profuse, violet purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

3 Drawing Sheets

Botanical classification:
Genus: *Clematis.*
Species: *viticella.*
Variety denomination: 'Evipo099'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo099' originated as a single seedling from the stated cross.

The new *clematis* plant may be distinguished from its female seed parent and male pollen parent by the following characteristics. The female seed parent has a growth height of 120 cm, while the new variety grows to 70 or 80 cm. The male seed parent has a growth height of 120 cm, while the new variety grows to 70 or 80 cm.

The objective of the hybridization of this *clematis* plant was to create a new and distinct variety for nursery culture with unique qualities such as:

1. Uniform and abundant violet purple flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo099' was selected by Mogens N. Olesen and Raymond J. Evison in their *clematis* development progam in the Channel Islands, United Kingdom in 2006. Asexual reproduction of 'Evipo099' by means of vegetative stem cuttings and traditional layering was first performed by Mogens N. Olesen and Raymond J. Evison in the Channel Islands United Kingdom nursery during the summer of 2006. This initial and subsequent asexual propagations have demonstrated that the characteristics of 'Evipo099' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo099'.

Specifically illustrated in FIG. 1 of the drawings shows an open flower viewed from the side and above, tepals detached, reproductive flower parts, and a flower bud.

DETAILED DESCRIPTION OF THE VARIETY

Figure 1:
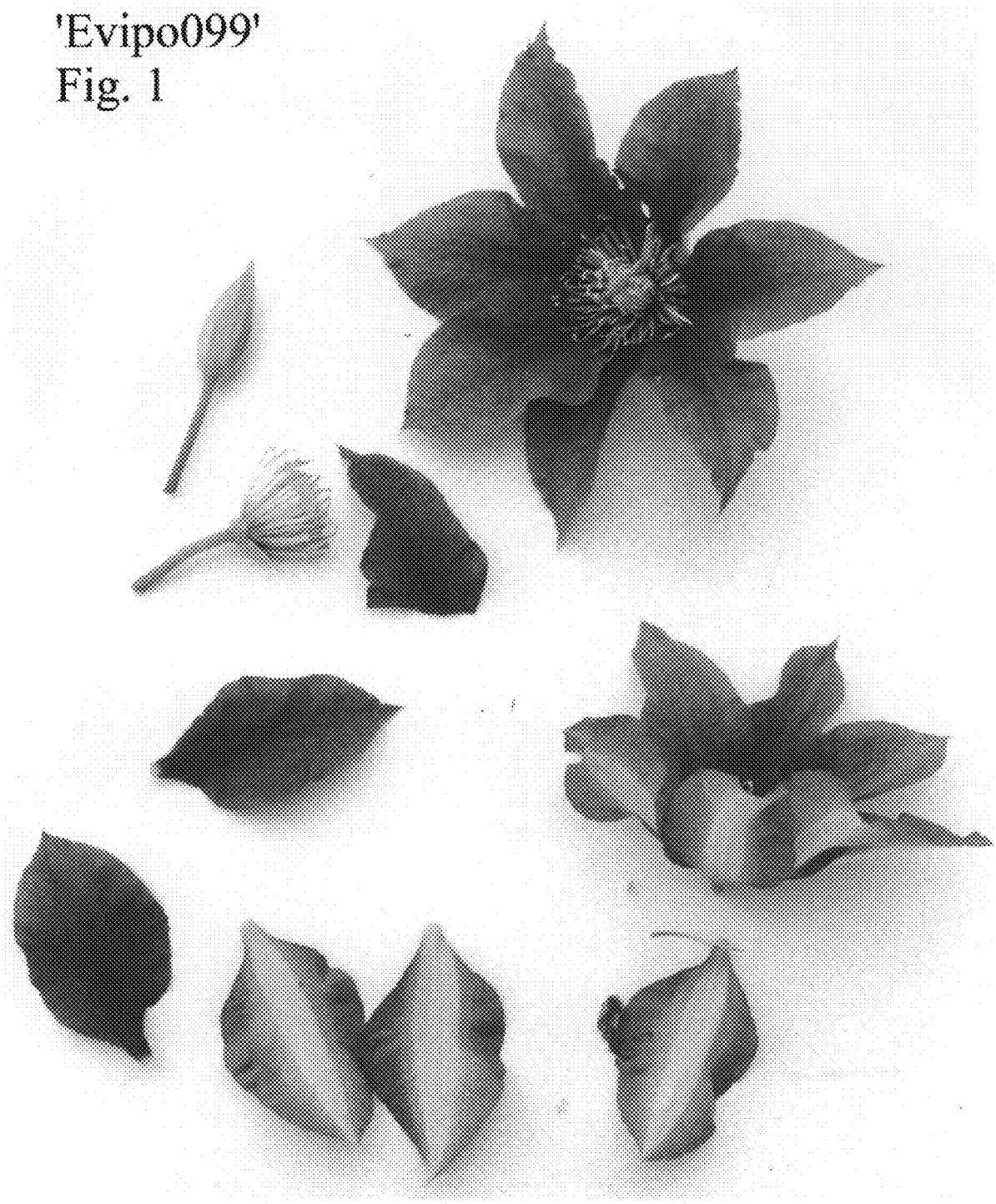
Figure 2:
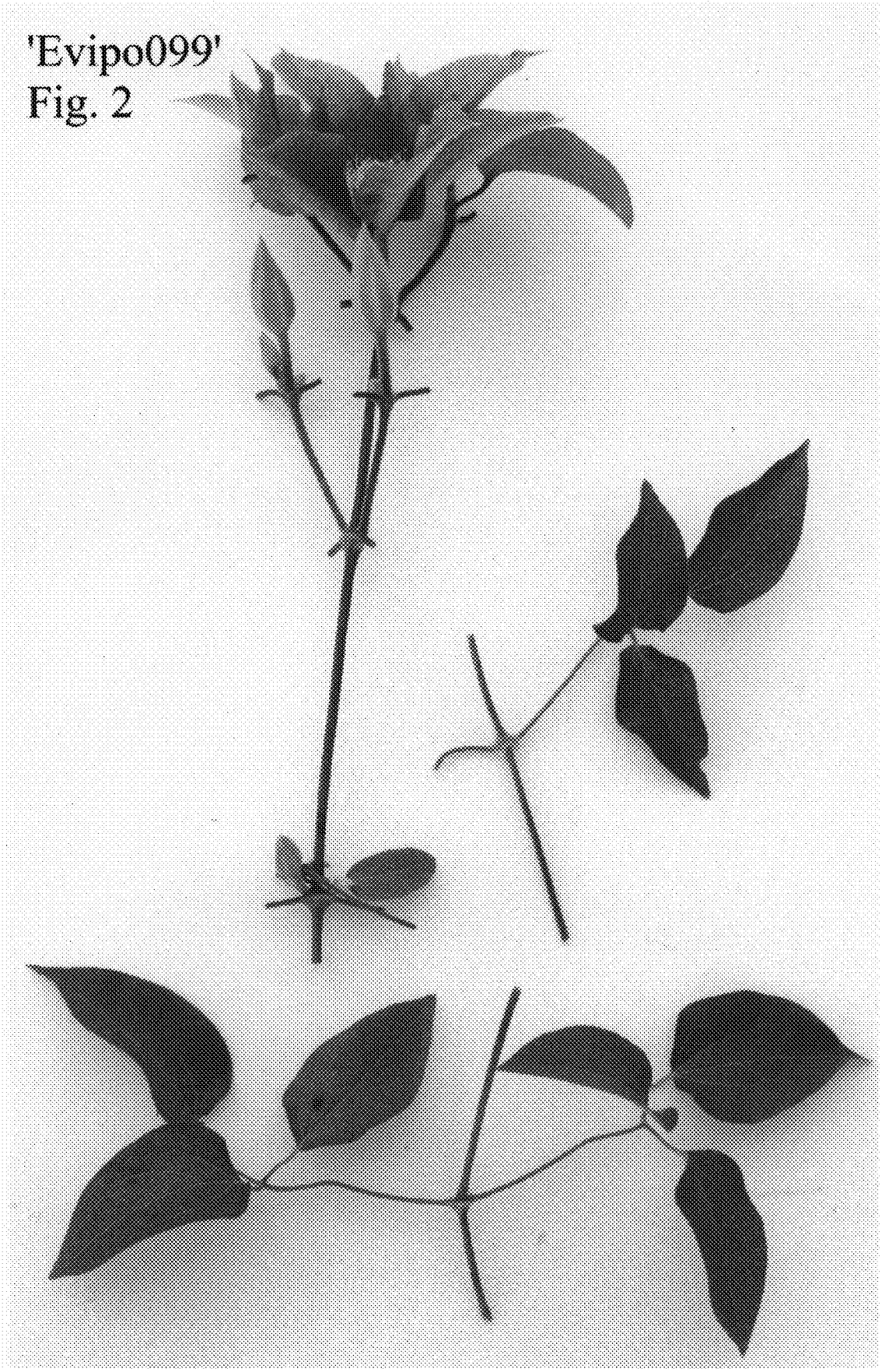
FIG. 2 shows a cluster of flowers on bare stem and leaves.
Figure 3:
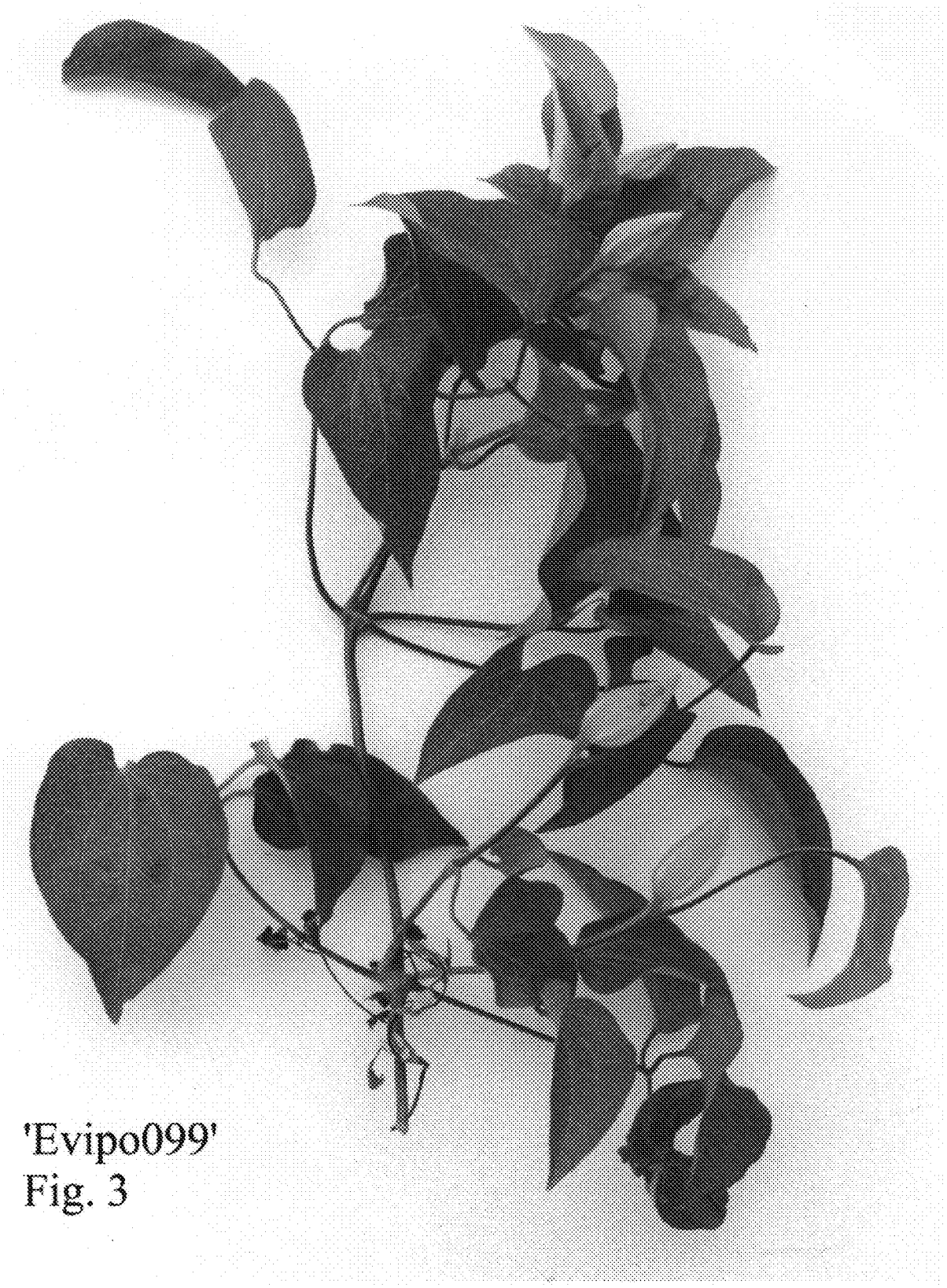
FIG. 3 shows a cluster of flowers on the branch with leaves. Illustrated plants are 2 years of age.

The following is a detailed description of 'Evipo099', as observed in its growth throughout the flowering period in Marion County Oreg. Observed plants were cultivated for a period of 24 months in an open field. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo023' described and illustrated in U.S. Plant Pat. No. 15,166 are compared to 'Evipo099' in Chart 1.

CHART 1

| | 'Evipo099' | 'Evipo023' |
|---|---|---|
| Flower diameter | 120 mm | 90 to 120 mm |
| Tepal upper surface after opening | Violet Blue Group 93B with a central bar intonation of Violet-Blue Group 93A | Violet-Blue Group 91A |
| Tepal count | 7 | 6 to 8 |

FLOWER AND FLOWER BUD

Blooming habit: Continuous. The natural flowering period is generally from April to September.

Flower bud:
- *Size*.—Normally 25 mm in length. Bud diameter is 10 mm.
- *Bud form*.—Elliptical.
- *Bud color*.—Yellow-Green Group 145B and 145C.
- *Texture*.—Pubescent.

Pedicel:
- *Surface texture*.—Lightly pubescent.
- *Length*.—On average 15 mm in length with 2 mm diameter.
- *Color*.—Yellow-Green Group 145B with intonations of Greyed-Orange Group 166A.
- *Strength*.—Moderately strong.

Receptacle:
- *Surface texture*.—Lightly pubescent.
- *Shape*.—Broad funnel.
- *Size*.—1 mm (h)×4 mm (w).
- *Color*.—Yellow-Green Group 145B.

Flower arrangement:
- *Location on vine*.—New and old growth.
- *Borne*.—Panicle fashion with 3 to 7 flowers in each cluster.

Flower bloom:
- *Size*.—On average, flowers are 120 mm in diameter and 35 mm in depth.
- *Profile*.—Open flowers are nearly flat.
- *Fragrance*.—None.
- *Lasting quality*.—Flowers normally remain up to 10 days on the plant.

Tepals:
- *Tepal color*.—The upper surface is Violet Blue Group 93B with a central bar intonation of Violet-Blue Group 93A. The lower surface is Violet-Blue Group 93C. Yellow-Green Group 14C at the central bar.
- *Quantity*.—Normally 7 tepals.
- *Size*.—About 55 mm in length by 33 mm wide.
- *Shape*.—Individual tepal shape is ovate. The tepal apex is acuminate. The tepal base is acute.
- *Apex recurvature*.—None.
- *Tepal cross section*.—Reflexed inward.
- *Margins*.—Entire with light undulations.
- *Persistence*.—Tepals drop off cleanly.

Reproductive organs:
- *Pollen*.—None observed.
- *Anthers*.—Size: 5 mm in length. Color: Greyed-White Group 156D. Quantity: On average, 40.
- *Filaments*.—Color: White Group 155A. Length: 10 mm.
- *Pistils*.—Quantity: On average, 20.
- *Stigmas*.—Level in location relative to the length of the filaments and the height of the anthers.
- *Styles*.—Color: Green-White Group 157A. Length: 10 mm.

Seed head characteristics: Seed not observed to date.

PLANT

Plant form: Climbing.

Plant growth: Compact, moderately vigorous.

Size: Seasons growth attains 70 to 80 cm in height. Average spread is 40 cm.

Stems:
- *Color*.—Juvenile stems are Yellow-Green Group 145B and Greyed-Orange Group 166A. Mature stems are Greyed-Orange Group 166A.
- *Internodes*.—On average, 8 cm between nodes.
- *Length*.—Normally 20 cm from the base of the plant to the flowering portion of the stem.
- *Diameter*.—About 3 mm.
- *Texture*.—Mature stems are ribbed.

Plant foliage:
- *Leaf characteristics*.—Deciduous.
- *Arrangement*.—Ternate.
- *Leaf size*.—Compound leaves are 120 to 170 mm (l)×100 mm (w). Leaflets are about 70 mm (l)×43 mm (w).
- *Abundance*.—On average 1 leaf per 10 cm of stem.
- *Leaf color*.—Juvenile upper Yellow-Green Group N144A with marginal intonations of Greyed-Orange Group 166A. Juvenile lower Juvenile upper Yellow-Green Group N144A with marginal intonations of Greyed-Orange Group 166A. Mature upper Yellow-Green Group 146A. Mature lower Yellow-Green Group 146B.
- *Stipules*.—Absent.
- *Petioles*.—Size: Normally 70 mm in length by mm diameter. Texture: Smooth. Color: Yellow-Green Group 144A with light intonations of Greyed-Red Group 179B.
- *Petioloule*.—Size: About 30 mm in length by 2 mm diameter. Texture: Smooth. Color: Yellow-Green Group 144A with light intonations of Greyed-Red Group 179B.
- *Leaflet shape*.—Ovate. The base is rounded or acute and the apex is acute.
- *Margin*.—Entire.
- *Surface*.—The upper side is smooth, the lower side is smooth.
- *Thickness*.—Moderate.
- *Glossiness*.—Somewhat glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo099', substantially as described and illustrated, due to its abundant violet purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo099'

'Evipo099'

'Evipo099'